United States Patent
Amberg et al.

(10) Patent No.: US 6,235,903 B1
(45) Date of Patent: May 22, 2001

(54) METHOD FOR PREPARING SULFANYL-TYPE ENDOTHELIN RECEPTOR ANTAGONISTS

(75) Inventors: Wilhelm Amberg, Schwetzingen; Rolf Jansen, Mannheim; Dagmar Klinge, Schriesheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,771
(22) PCT Filed: Feb. 25, 1999
(86) PCT No.: PCT/EP99/01209
§ 371 Date: Aug. 23, 2000
§ 102(e) Date: Aug. 23, 2000
(87) PCT Pub. No.: WO99/44988
PCT Pub. Date: Sep. 10, 1999

(30) Foreign Application Priority Data

Mar. 6, 1998 (DE) ................................. 198 09 635

(51) Int. Cl.$^7$ ................................. C07D 239/02
(52) U.S. Cl. ................. 544/302; 544/298; 544/318; 544/299
(58) Field of Search .................. 544/302, 298, 544/299, 318

(56) References Cited

FOREIGN PATENT DOCUMENTS

94/25442  11/1994  (WO) .
95/26716  10/1995  (WO) .
96/11914   4/1996  (WO) .

*Primary Examiner*—Joseph K. McKane
*Assistant Examiner*—Joseph Murray
(74) *Attorney, Agent, or Firm*—Keil & Weinkauf

(57) ABSTRACT

A process for preparing endothelin receptor antagonists of the sulfanyl type of the general formula I

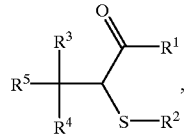

by nucleophilic reaction of a carboxylic acid derivative of the formula II with a sulfide of the formula III

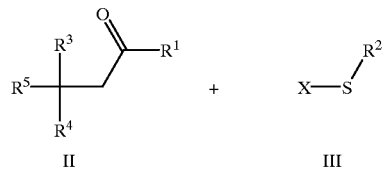

to give endothelin receptor antagonists of the formula I.

5 Claims, No Drawings

METHOD FOR PREPARING SULFANYL-TYPE ENDOTHELIN RECEPTOR ANTAGONISTS

This application is a 371 of PCT/EP99/01209 filed Feb. 25, 1999.

The present invention relates to a novel process for preparing carboxylic acid derivatives of the general formula I

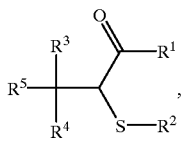

where $R^1$ is hydroxyl, alkoxy, sulfonamidyl, amino, $R^2$ is alkyl, aryl or hetaryl, optionally substituted, $R^3$, $R^4$, $R^5$ are identical to or different from one another and are alkyl or aryl, optionally substituted.

Substances of the general formula I are disclosed in WO 94/25442, WO 95/26716 and WO 96/11914. These substances have in some cases a herbicidal effect and sometimes also affinity for endothelin receptors.

These substances are prepared by nucleophilic substitution of a leaving group in the a position of the corresponding carboxylic acid derivative by a thiol.

However, this mode of preparation is unsatisfactory in terms of the yield.

It is an object of the present invention to provide alternative processes for preparing carboxylic acid derivatives of the general formula I.

Seebach et al. (Journal Am. Soc 105, 1983, pp. 5390) describe the following reaction which makes it possible to introduce a thioether in 81% [lacuna] into the a position of a lactone.

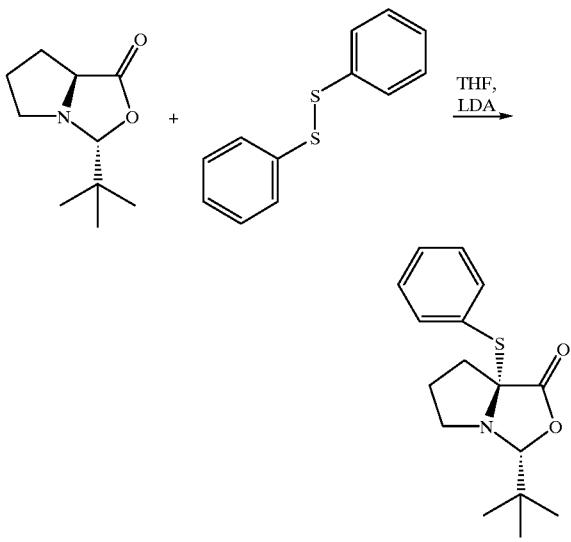

The invention relates to a process for preparing carboxylic acid derivatives of the general formula I

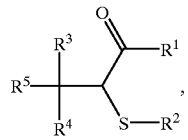

where $R^1$ [sic] is hydroxyl, alkoxy, sulfonamidyl, amino, $R^2$ [sic] is alkyl, aryl or hetaryl, optionally substituted, $R^3$, $R^4$, $R^5$ are identical to or different from one another and are alkyl or aryl, optionally substituted, by nucleophilic reaction of a carboxylic acid derivative of the formula II with a sulfide of the formula III

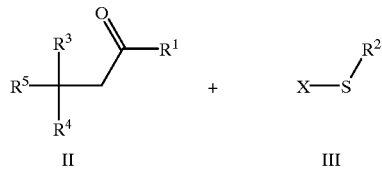

where x is $SR^6$ or $SO_2R^6$, $R^6$ is alkyl or aryl, optionally substituted.

The carboxylic acid derivatives of the formula II are disclosed in WO 97/09294 or can be prepared from known precursors.

The preparation of the sulfides III is disclosed in, for example, Heckel et al., Helv. Chim. Acta 69, 1986; Harpp et al. J. Org. Chem. 35, 1970, 3259, and normally takes place by oxidizing the corresponding thiols, for example with iodine. The sulfides III preferably employed are symmetrical diaryl disulfides and dihetaryl disulfides.

Good results can be obtained when suitably strong bases are employed for deprotonating the ester or the acid in the a position, such as, for example, LDA or NaH, in a solvent suitable for this type of reaction, such as THF, dioxane or ether.

The base is normally employed in a molar excess based on the carboxylic acid derivatives II, and preferably 2 mol of base are employed per mole of II.

If further acidic protons are present in II, correspondingly more base must be employed.

The diaryl disulfide component is generally employed in 1–10, preferably 1–3, equivalents.

The reaction can be carried out in a temperature range between −80° C. and up to +100° C., preferably at −78° C. to room temperature. Reaction temperatures outside this range result in no particular advantages for the yield.

EXAMPLE 1

General method 12 ml of a 1.5 M lithtium [sic] diisopropylamide solution (if further acidic protons are present in the molecule, the number of base equivalents must be increased correspondingly) were added to a solution of 9 mmol of a carboxylic acid derivative of the formula II, dissolved in 15 ml of THF, at −78° C. The solution was warmed to −30° C. and then stirred for one hour. It was subsequently cooled to −78° C. again, and 9 mmol of a diaryl disulfide dissolved in 10 ml of THF were added. The solution was warmed to room temperature and stirred for 16 hours. Subsequently a phosphate buffer (pH=7.0) was added and the THF was distilled out in vacuo. The residue was taken up in water/ethyl acetate, and the aqueous phase was extracted with ethyl acetate. The collected organic phases were washed with 10% NaOH solution and, after drying, the solvent was distilled off. The oily residue was purified by flash chromatography, and the product was isolated as a pale yellow solid.

EXAMPLE 2

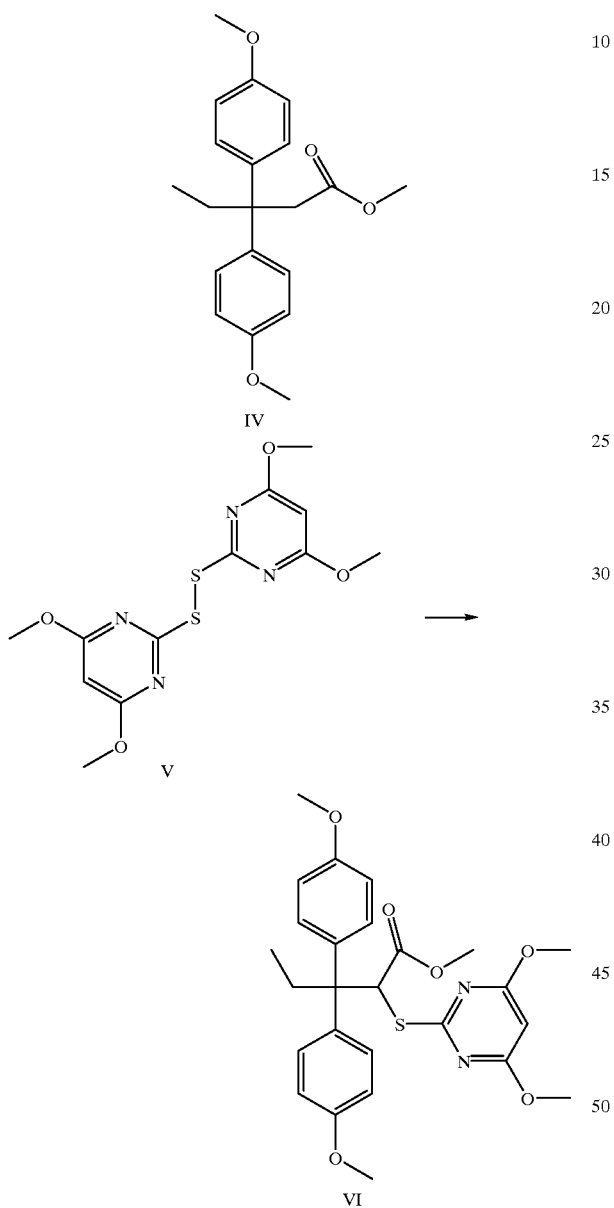

12 ml of a 1.5 M lithtium [sic] diisopropylamide solution were added to a solution of 2.95 g (9 mmol) of the methyl ester of the formula IV, dissolved in 15 ml of THF, at −78° C. The solution was warmed to −30° C. and then stirred for one hour. It was subsequently cooled to −78° C. again, and 3 g (9 mmol) of di(2-(4,6-dimethoxypyrimidyl)) [sic] disulfide (V) dissolved in 10 ml of THF were added. The solution was warmed to room temperature and stirred for 16 hours. Subsequently a phosphate buffer pH=7.0 was added and the THF was distilled off in vacuo. The residue was taken up in water/ethyl acetate and the aqueous phase was extracted with ethyl acetate. The collected organic phases were washed with 10% NaOH solution and, after drying, the solvent was distilled off. The oily residue was purified by flash chromatography, and 3 g (about 66%) of the product VI were isolated as a pale yellow solid.

Further examples prepared by the general method:

3) Methyl 3,3-diphenyl-2-(4,6-dimethoxypyrimidine-2-sulfanyl)propionate
4) Methyl 3,3-diphenyl-2-(4,6-dimethoxypyrimidine-2-sulfanyl)butanoate
5) Methyl 3,3-di(4-methoxyphenyl)-2-(4,6-dimethoxypyrimidine-2-sulfanyl)pentanoate
6) Methyl 3,3-di(4-methoxyphenyl)-2-(4,6-dimethylpyrimidine-2-sulfanyl)pentanoate
7) Methyl 3,3-di(4-methoxyphenyl)-2-(4,6-dimethoxypyrimidine-2-sulfanyl)butanoate
8) Methyl 3,3-diphenyl-2-(4-methoxy-6-methylpyrimidine-2-sulfanyl)butanoate
9) Methyl 3,3-diphenyl-2-(4,6-dimethylpyrimidine-2-sulfanyl)butanoate
10) Methyl 3,3-di(4-methoxyphenyl)-2-(benzo-1,3-dioxol-5-ylsulfanyl)pentanoate
11) Methyl 3,3-diphenyl-2-(benzo-1,3-dioxol-5-ylsulfanyl)butanoate

We claim:

1. A process for preparing carboxylic acid derivatives of the general formula I

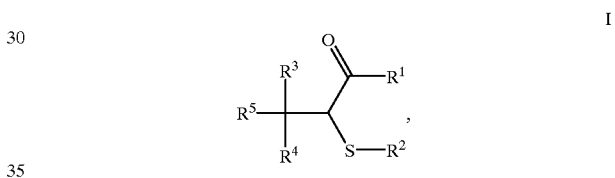

where
$R^1$ is hydroxyl, alkoxy, sulfonamidyl, amino,
$R^2$ is alkyl, aryl or hetaryl, optionally substituted,
$R^3$, $R^4$, $R^5$ are identical to or different from one another and are alkyl or aryl, optionally substituted,
by nucleophilic reaction of a carboxylic acid derivative of the formula II with a sulfide of the formula III

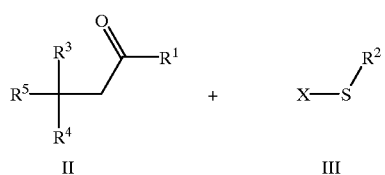

where
X is $SR^6$ or $SO_2R^6$,
$R^6$ is alkyl or aryl, optionally substituted.

2. A process as claimed in claim 1, wherein the carboxylic acid derivative of the formula II is deprotonated with a base in an inert solvent.

3. A process as claimed in claim 1, wherein the disulfide III is employed in an amount of 1–10 equivalents based on II.

4. A process as claimed in claim 1, wherein the reaction is carried out at a temperature from −100 to +1000° C.

5. A process as claimed in claim 1, wherein a disulfide of the formula $R^2$—S—S—$R^2$ is employed as sulfide III.

* * * * *

UNITED STATES PATENT AND TRADEMARK OFFICE
CERTIFICATE OF CORRECTION

| | |
|---|---|
| PATENT NO. | : 6,235,903 B1 |
| APPLICATION NO. | : 09/622771 |
| DATED | : May 22, 2001 |
| INVENTOR(S) | : Amberg et al. |

Page 1 of 1

It is certified that error appears in the above-identified patent and that said Letters Patent is hereby corrected as shown below:

<u>Column 4, claim 4,</u>
Line 63, "+1000°C" should be -- +100°C --.

Signed and Sealed this

Twenty-second Day of August, 2006

JON W. DUDAS
*Director of the United States Patent and Trademark Office*